United States Patent [19]

Lindstrom

[11] Patent Number: 4,851,003
[45] Date of Patent: Jul. 25, 1989

[54] CORNEAL IMPLANT LENS WITH FIXATION HOLES

[76] Inventor: Richard L. Lindstrom, 20050 Lakeview Ave., Excelsior, Minn. 55331

[21] Appl. No.: 141,117

[22] Filed: Jan. 5, 1988

[51] Int. Cl.$^4$ .................................................. A61F 2/14
[52] U.S. Cl. ........................................... 623/5; 427/2
[58] Field of Search .................. 623/46, 66; 427/2

[56] References Cited

U.S. PATENT DOCUMENTS

| 2,714,721 | 8/1955 | Stone, Jr. ........................... 623/5 |
| 4,589,881 | 5/1986 | Pierschbacher et al. ......... 623/66 X |
| 4,624,669 | 11/1986 | Grendahl ............................ 623/5 |
| 4,731,079 | 3/1988 | Stoy .................................... 623/6 |

FOREIGN PATENT DOCUMENTS 2705234 8/1978 Fed. Rep. of Germany .......... 623/5

OTHER PUBLICATIONS

"Epikeratophakia in Very Young Babies", by K. S. Morgan, AMO Kerato-Lens TM Update, vol. 2, No. 2, Aug. 1985, 623-5, 4 pages.

Primary Examiner—Ronald L. Frinks
Attorney, Agent, or Firm—Hugh D. Jaeger

[57] ABSTRACT

Intracorneal or epicorneal lens with a plurality of fixation holes spaced about the outer circumference of the lens. The lens can be of a soft material, such as hydrogel, a high refractive index material such as polysulfone, polycarbonate, or polyethylene, or any other material. The lens can also be coated with any suitable material, such as hydrogel or glycosaminoglycan.

6 Claims, 6 Drawing Sheets

CORNEAL IMPLANT LENS WITH FIXATION HOLES

BACKGROUND OF THE INVENTION

1. Field of the Invention

The present invention pertains to lenses for the eye, and more particularly, pertains to an intracorneal or epicorneal lens with fixation holes for fixation of the lens to the corneal stroma.

2. Description of the Prior Art

Prior art intracorneal and epicorneal lenses have not currently addressed the issues of fixation within and about the cornea. The lenses in the past have just been positioned within the corneal stroma or between the epithelium and the corneal stroma, and have been expected to maintain appropriate placement without shifting position.

The present invention provides fixation holes for assuring the fixation of the intracorneal or the epicorneal lens within and about the cornea.

SUMMARY OF THE INVENTION

The general purpose of the present invention is to provide fixation holes for a corneal implant lens such as an intracorneal or an epicorneal lens.

According to one embodiment of the present invention, there is provided an optic of a soft or hard high refractive index material, and a plurality of fixation holes positioned about an outer circumference of the optic. The optic can be either a intracorneal lens or an epicorneal lens. The optic can be a hydrogel material or a like synthetic material or a hard high refractive index material such as polysulfone or polycarbonate.

One significant aspect and feature of the present invention is a intracorneal lens with fixation holes.

Another significant aspect and feature of the present invention is an epicorneal lens with fixation holes.

Having thus described the embodiments of the present invention, it is the principal object hereof to provide fixation holes for a intracorneal or an epicorneal lens.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
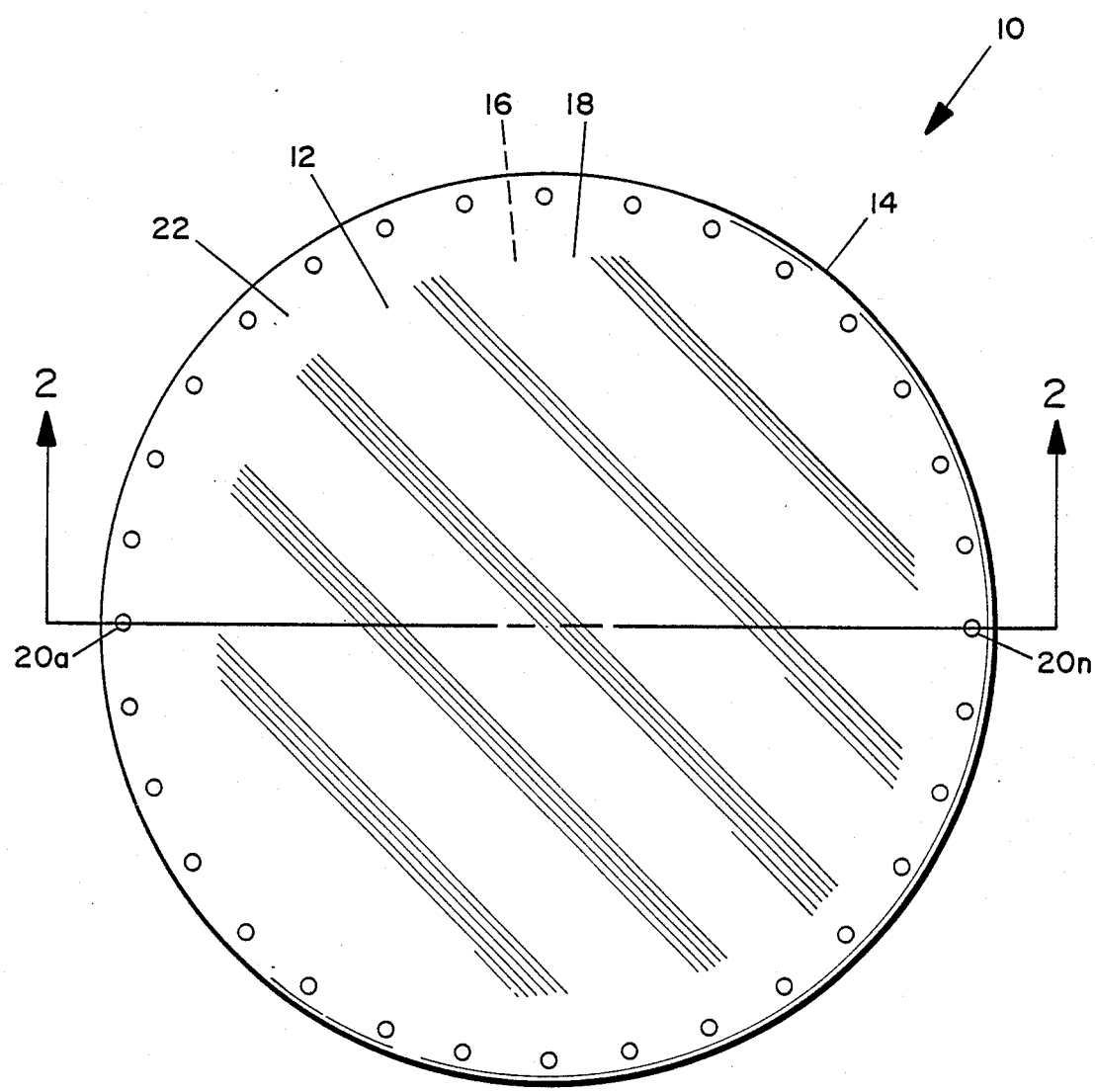
FIG. 1 illustrates a top view of an intracorneal lens.

FIG. 1 illustrates a top view of an intracorneal lens 10, including a high refractive index polymer optic 12, an edge 14, a posterior surface 16, and an anterior surface 18. The intracorneal lens 10 can be made of a synthetic biocompatible material, such as a hydrogel, polysulfone, or polycarbonate. The intracorneal lens is provided with a plurality of fixation holes 20a-20n about the peripheral circumference of the edge 14 as illustrated in the figure. The holes 20a-20n can be in a range of 1 micrometer to 1 mm and spaced accordingly. While the holes 20a-20n are illustrated as being round, the holes can assume any geometrical configuration, such as slits, ovals, or like configurations. A basement coating membrane material 22, such as hydrogel, fibronectin, laminen, glycosaminoglycan or type IV Collagen or like material can be coated over the lens optic 12 and provides for growth of the epithelium over the anterior surface 18 of the lens optic 12.

Figure 2:
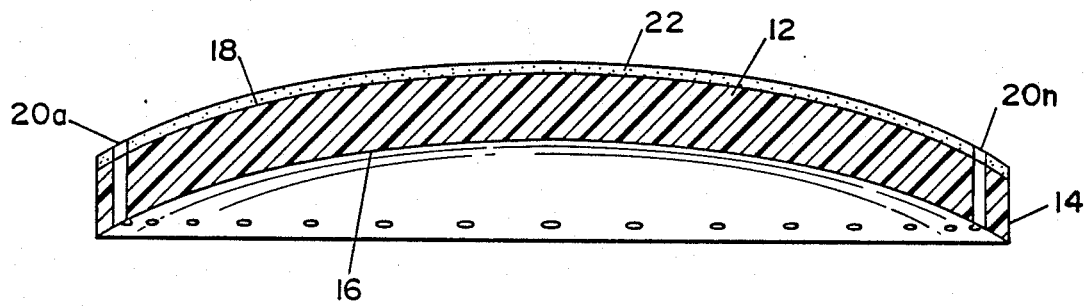
FIG. 2 illustrates a cross-sectional side view of an intracorneal lens taken along line 2—2 of FIG. 1.

FIG. 2 illustrates a view taken along line 2—2 of FIG. 1 where all numerals correspond to those elements previously described.

MODE OF OPERATION

Figure 3:
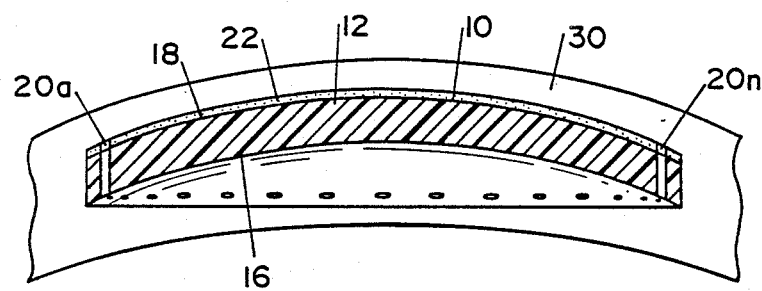
FIG. 3 illustrates a side view of an intracorneal lens implanted in the cornea.

FIG. 3 illustrates the intracorneal lens 10 implanted in the corneal stroma 30 of an eye. The fixation holes 20a-20n provide for tissue ingrowth accordingly.

Figure 4:
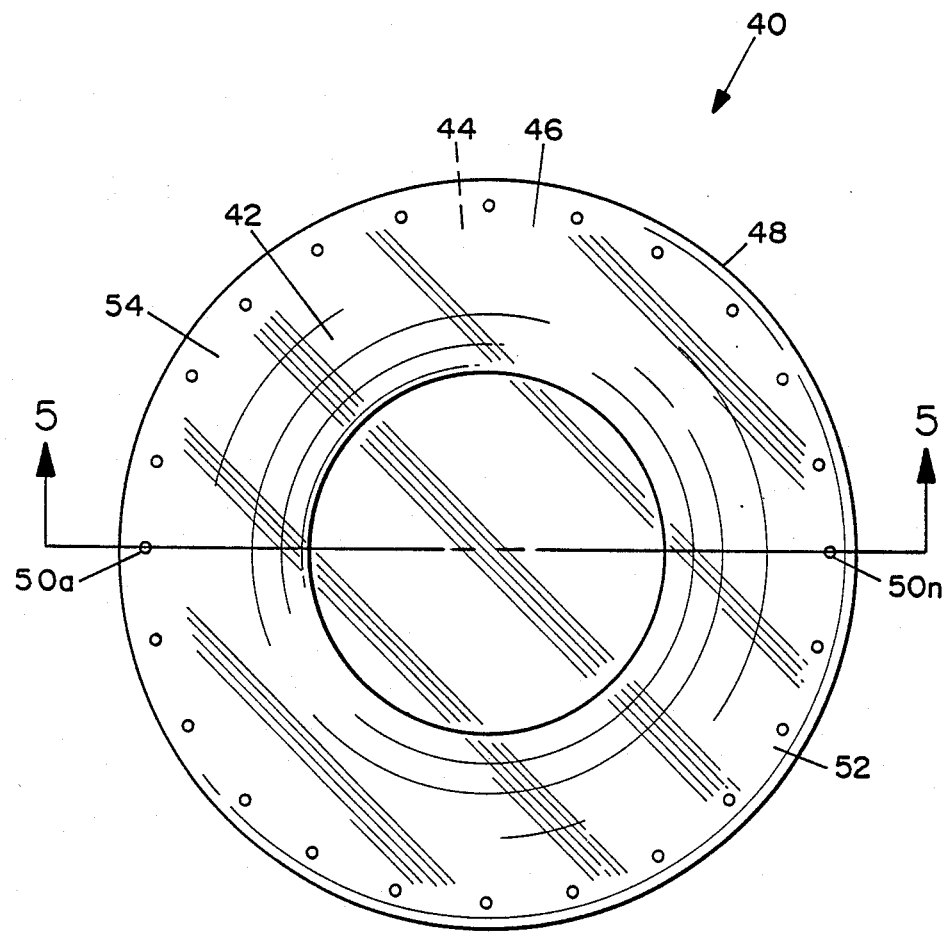
FIG. 4 illustrates a top view of an epicorneal lens.

FIG. 4 illustrates a top view of a synthetic epicorneal lens 40, including a high refractive index polymer, optic 42, a posterior surface 44, an anterior surface 46, an edge 48 and a plurality of fixation holes 50a-50n about the peripheral circumference of the edge 48 as illustrated in the figure. The lens 40 is of a synthetic biocompatible material including such materials as polymers, hydrogel, silicone, fluoropolymer, cellulose acetate butyrate, polysulfone, polycarbonate or other like materials which are gas permeable, metabolite permeable, or fenestrated. The optic 42 of the lens 40 is provided with a radius of curvature to provide for appropriate conformance to the cornea, or in the alternative, for providing support and shaping of the cornea for correcting the specific refractive condition which includes aphakia, myopia, and keratoconus. The lens optic 42 conforms to the top surface of the stroma and includes a taper 52 terminating at the edge 48 for accommodation in a surgical slit as described in FIG. 6. The lens 40 also includes an optic shape as illustrated dependant upon the particular circumstances of implant. The specific thickness, as well as curvature of the lens optic 42, is determined for the particular epikeratophakia condition which determines the thickness of the lens 40, the curvature of the lens 40, and the specific edge structure of the lens 40. A basement coating membrane material 54 such as hydrogel, fibronectin, laminen, glycosaminoglycan, or Type IV collagen or the like material can be coated over the lens optic 42, and provides for growth of the epithelium over the anterior surface 46 of the lens 40. A plurality of holes 50a-50n surround the peripheral circumference of the optic 42 and are in a range of 1 micrometer to 1 mm and spaced accordingly. The holes 50a-50n are illustrated as being round. The holes can assume any geometrical configuration such as slits, ovals, or like configurations.

Figure 5:
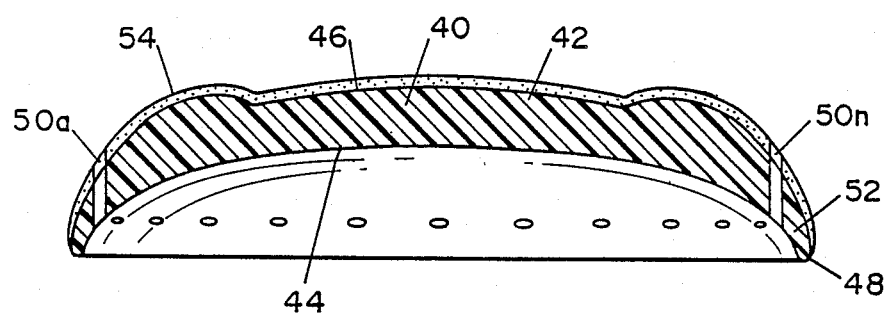
FIG. 5 illustrates a cross-sectional side view of an epicorneal lens taken along line 5—5 of FIG. 4; and, FIG. 6 illustrates a view of the epicorneal lens implanted below the epithelium.

FIG. 5 illustrates a side view of the lens 40 where all numerals correspond to those elements previously described. Particularly illustrated is the basement membrane material 54 coating the anterior surface 46 of the lens 40, as well as about the edge 48 of the lens 40. It is only necessary to provide a minimal coating over the area where the epithelium is to grow over the top surface of the lens optic 42, but it may be desirable to coat a larger area of the lens optic 42 as so desired. The basement membrane coating 54 provides that the epithelium grows over and adheres to the anterior surface 46 of the lens optic 42. The growth of the epithelium is either through the nature of the material or through the basement membrane coating 54 over the lens optic 42 such as by the basement membrane material 54. The lens optic 42 is configured as previously discussed to be accommodated in the cornea and as later described in detail. The edge 48 includes a taper 52 for purposes of accommodation in a tight seal in the cornea.

MODE OF OPERATION

Figure 6:
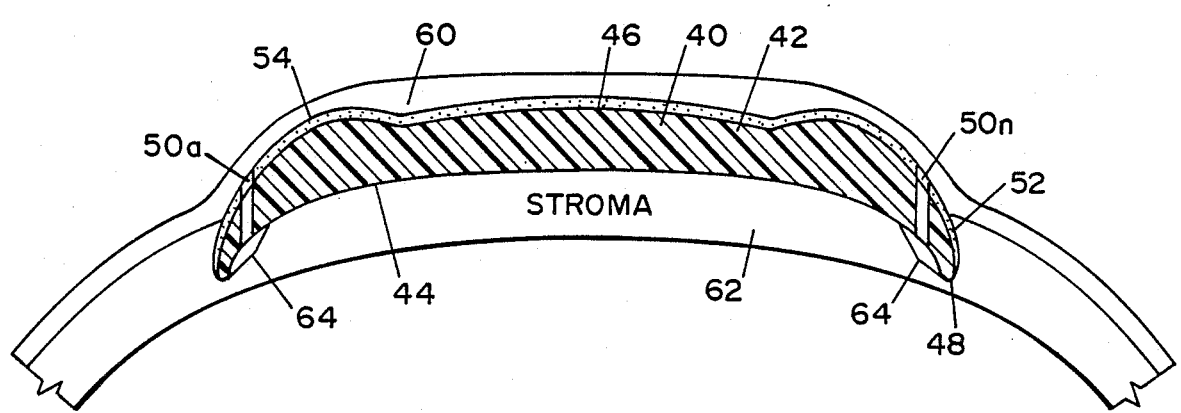

FIG. 6 illustrates the lens 40 applied under the cornea 60 and about the stroma 62. The surgical technique for implanting the lens 40 is that used in the technique of epikeratophakia which includes removing the epithelium, and creating the annular keratotomy. The edge 48 is inserted into an incision 64 providing a tight seal about the continuous ring through the use of surgical biocompatible broad-base adhesive. The particular geometrical structure of the lens optic 42 is determined by the desired correction in the eye. Subsequently, the basement membrane material 54 provides for and enhances growth of the epithelium over the lens optic 42. The placement of the lens is on top of the stroma 62 and under the corneal epithelium 60. The fixation holes 50a-50n provide for tissue ingrowth, securing the lens 40 in position.

Various modifications can be made to the present invention without departing from the apparent scope hereof.

I claim:

1. A corneal implant lens comprising an optic having a plurality of fixation holes about a periphery, the optic including a coating of a material which enhances the growth of corneal epithelium cells into and about said holes.

2. The lens of claim 1 wherein the coating material is selected from the group of fibronectin, laminen, a glycosaminoglycan or a type IV collagen.

3. The lens of claim 2 wherein the coating is on the anterior surface of the lens.

4. A method for enhancing the growth and adhesion of corneal epithelium cells to a corneal implant lens implanted in the cornea, the method comprising providing the lens with a plurality of fixation holes about its periphery, and a coating of a material which enhances the growth of corneal epithelium cells into and about said holes.

5. The method of claim 4 wherein the material is selected from the group of fibronectin, laminen, a glycosaminoglycan or a tyoe IV collagen.

6. The method of claim 5 wherein the material is coated on the anterior surface of the lens.

* * * * *